(12) United States Patent
Auvray et al.

(10) Patent No.: US 11,191,933 B2
(45) Date of Patent: Dec. 7, 2021

(54) DEVICE FOR DETECTING A MALFUNCTIONING OF A VENTRICULOPERITONEAL SHUNT FOR CEREBROSPINAL FLUID

(71) Applicant: Neurallys, Paris (FR)

(72) Inventors: Philippe Auvray, Caen (FR); Etienne Mireau, Paris (FR)

(73) Assignee: Neurallys

( * ) Notice: Subject to any disclaimer, the term of this patent is extended or adjusted under 35 U.S.C. 154(b) by 515 days.

(21) Appl. No.: 16/315,836

(22) PCT Filed: Jul. 7, 2017

(86) PCT No.: PCT/EP2017/067058
§ 371 (c)(1),
(2) Date: Jan. 7, 2019

(87) PCT Pub. No.: WO2018/007574
PCT Pub. Date: Jan. 11, 2018

(65) Prior Publication Data
US 2019/0307997 A1    Oct. 10, 2019

(30) Foreign Application Priority Data

Jul. 7, 2016  (FR) ...................... 1656564

(51) Int. Cl.
*A61M 27/00*   (2006.01)
*A61B 5/03*    (2006.01)
*A61B 5/00*    (2006.01)

(52) U.S. Cl.
CPC .......... *A61M 27/006* (2013.01); *A61B 5/031* (2013.01); *A61B 5/0004* (2013.01); *A61B 5/0022* (2013.01);

(Continued)

(58) Field of Classification Search
CPC ............. A61M 27/006; A61M 27/002; A61M 2205/3331; A61M 2205/3523; A61B 5/031; A61B 5/0004; A61B 5/0022
See application file for complete search history.

(56) References Cited

U.S. PATENT DOCUMENTS

2007/0208293 A1   9/2007  Mansour et al.
2008/0139959 A1   6/2008  Miethke et al.
(Continued)

FOREIGN PATENT DOCUMENTS

EP     2090330 A1    8/2009
WO   2015109260 A1   7/2015

OTHER PUBLICATIONS

Preliminary Search Report including Written Opinion for French Application No. 1656564 dated Mar. 3, 2017.

(Continued)

*Primary Examiner* — Philip R Wiest
(74) *Attorney, Agent, or Firm* — Lerner, David, Littenberg, Krumholz & Mentlik, LLP (57) ABSTRACT

The invention relates to a device for detecting a malfunctioning of a valve/catheters assembly for shunting a cerebrospinal fluid or the like, characterized in that it comprises: a chamber (6) which is placed inside the said housing; a laminar canal (4), a sensor (7) for measuring a pressure in the said chamber; a flexible membrane (5) separating the sensor from the chamber (6); control and communications electronics (8,9) able to exchange with an external reader in order to transmit a measurement by the said sensor, the sensor (7) being attached to the flexible membrane (5) with which it is in contact.

13 Claims, 12 Drawing Sheets

(52) U.S. Cl.
CPC ............... *A61M 2205/3331* (2013.01); *A61M 2205/3523* (2013.01)

(56) References Cited

U.S. PATENT DOCUMENTS

| | | |
|---|---|---|
| 2014/0243703 A1 | 8/2014 | Schmidt et al. |
| 2014/0276346 A1 | 9/2014 | Sadanand |
| 2016/0331949 A1* | 11/2016 | Lutz ...................... A61B 5/031 |

OTHER PUBLICATIONS

International Search Report for PCT/EP2017/067058 dated Sep. 11, 2017.

* cited by examiner

DEVICE FOR DETECTING A MALFUNCTIONING OF A VENTRICULOPERITONEAL SHUNT FOR CEREBROSPINAL FLUID

CROSS-REFERENCE TO RELATED APPLICATIONS

The present application is a national phase entry under 35 U.S.C. § 371 of International Application No. PCT/EP2017/067058, filed Jul. 7, 2017, which claims priority from French Patent Application No. 1656564, filed Jul. 7, 2016, all of which are incorporated herein by reference.

GENERAL TECHNICAL FIELD AND PRIOR ART

The present invention relates to the field of shunt valves and more particularly those used in cases of hydrocephalus treatment.

It advantageously finds application in the case of ventriculoperitoneal valves.

Hydrocephalus is a pathology that affects a large number of patients and that may have different causes: congenital cause, congenital cause in relation to the Zika virus, brain tumor, result of severe head trauma (from fall, accident), perturbation in the cerebrospinal fluid (CSF) regulation system, etc.

This pathology generates different types of disorders: headache, nausea, consciousness disturbance, visual disorders, comas or even deaths due to generated intracranial hypertension.

The main known treatment consists in implanting on the patient a ventriculoperitoneal shunt composed of two catheters and a valve which regulates the intracranial pressure and allows the flow of CSF which is produced continuously in the brain at a 21 ml/h rate.

These valves, however, experience disturbances and/or malfunctions which are sometimes related to infections or changes in the biochemical composition of CSF and must therefore often be replaced: 40% of implants are replaced after two years, 98% after ten years.

In addition, diagnoses of valve malfunctions are often difficult and time-consuming, requiring sometimes unnecessary exploratory surgeries to check the proper operation of the valve-catheters assembly, which is not satisfactory given the serious consequences that these disturbances can have on health and on patients' living conditions. In addition, when the patient's state of health does not improve after several surgical operations, doctors then use intraparenchymal probes (which are highly invasive in the brain) requiring hospitalization, to measure intracranial pressure and issue a diagnosis.

An implantable intracranial pressure measuring device is already known by the application US2008/0139959.

The cerebrospinal fluid circulates in a chamber which is separated, by a flexible membrane, from a measuring chamber where the pressure sensor is located.

GENERAL PRESENTATION OF THE INVENTION

The invention provides a solution allowing to detect malfunction of a ventriculoperitoneal shunt valve and catheters associated thereto, by means of a direct and ambulatory measurement of the intracranial pressure, which measurement is triggered either by the patient himself/herself or by a practitioner.

The diagnosis of a "shunt" malfunction cannot be done by means of a spot measurement but by multiple acquisitions over a period of time ranging from a few days to several weeks.

In particular, a general aim of the invention is to propose a device allowing better detection and prevention of possible malfunctions of an intracranial valve and associated catheters.

Another aim of the invention is to propose a solution that minimizes the risks of possible deposits (cell or protein debris contained in the CSF) at the chamber of which pressure is measured and in which the cerebrospinal fluid circulates.

Yet another aim of the invention is to propose a malfunction detection device allowing perfect insulation of the pressure sensor and of the electronic portion from the cerebrospinal fluid circulation circuit.

Another aim is also to propose a solution allowing to intervene on the electronics of the device, in particular to replace it, without having to interrupt and open the cerebrospinal fluid circulation circuit and intervene thereon.

Thus, the invention proposes a device for detecting malfunction of a valve/catheters assembly for shunting a cerebrospinal fluid, characterized in that it includes:
   a chamber;
   a laminar channel which opens into said chamber, on its both sides, and which is adapted to ensure circulation of a shunted fluid upstream of a valve, through said chamber;
   a pressure measuring sensor for measuring a pressure in said chamber;
   a flexible membrane which separates the sensor from the chamber;
   a control and communication electronics able to exchange with an external reader in order to transmit a measurement by said sensor,
   characterized in that the sensor is added onto the flexible membrane with which it is in contact.

It should be noted that such a structure allows measuring the pressure into the chamber in which the cerebrospinal fluid circulates with a better sensitivity than with the prior art.

The flexible membrane may be a silicone and/or parylene based material.

The membrane and/or the inner walls of the chamber may be covered with parylene and/or PTFE.

The membrane can cover the totality of the walls of the chamber.

The chamber may have general rounded shapes devoid of angle.

It should be noted that the various characteristics above contribute to a pressure measurement without disrupting the flow of the cerebrospinal fluid and by limiting the risks of cell or protein deposit and thus of obstruction in the chamber.

In one embodiment, the chamber is arranged inside a housing made of a biocompatible material, the laminar channel being adapted for a connection of said housing to shunt catheters, upstream of the valve.

Alternatively, the chamber (such as the sensor and all or part of the electronics) can be integrated with the valve in the same flexible enclosure or the same housing, to form a single assembly.

Also, the invention proposes an assembly including such a device and a very compact and therefore portable reader adapted to communicate with the control and communication electronics of the sensor.

In this way, there is a technical solution for ambulatory and autonomous measurement of the pressure of the shunted fluid upstream of the valve.

Such a device allows for example a person bearing a valve to detect by himself/herself malfunction of his/her valve with which he/she is implanted and to regularly make soundings and recordings that can be, when appropriate, subsequently submitted to surgeons for analysis.

The device is further completed with the following different characteristics taken alone or in all their technically possible combinations:
- it includes a titanium layer interposed between the flexible membrane and the sensor;
- an incompressible inert material is interposed between the flexible membrane and a membrane of the sensor;
- a pin or a gel is interposed between the flexible membrane and a membrane of the sensor;
- the control and communication electronics can be mounted/demounted independently of the chamber and is adapted for a mounting/demounting without interruption of the cerebrospinal fluid circulation;
- the chamber is arranged in a shell extending in a housing, said housing being adapted to be mounted on a housing receiving the control and communication electronics;
- the shell is traversed by a hole arranged in said shell to the right of the membrane, said hole receiving the pressure sensor;
- the sensor is mounted on a rigid board which extends, on one side, inside the housing receiving the shell of the chamber and, on the other side, outside said housing, said rigid board having, on its portion outside said housing, contacts for the electronic connection with the housing receiving the control and communication electronics;
- both housings include spikes and complementary guide/foolproof orifices;
- the sensor is a piezoelectric and/or piezoresistive sensor;
- the control and communication electronics include an amplification electronics, the measurement by the sensor being a passive measurement;
- the control electronics includes a resonantly-biasing electronics, the measurement by the sensor being a dynamic measurement;
- the control and communication electronics includes an inductive power system;
- the control and communication electronics includes a rechargeable cell or battery;
- the device further includes at least another sensor for the analysis of the fluid circulating in the circulation channel;
- the housing is made of titanium or ceramic;
- the housing includes a ceramic window to allow passage of the electromagnetic waves.

PRESENTATION OF THE FIGURES

Other characteristics and advantages of the invention will become apparent from the following description which is purely illustrative and not restrictive, and should be read with reference to the appended figures wherein.

DESCRIPTION OF ONE OR SEVERAL MODE(S) OF IMPLEMENTATION AND EMBODIMENT(S)

Figure 1:
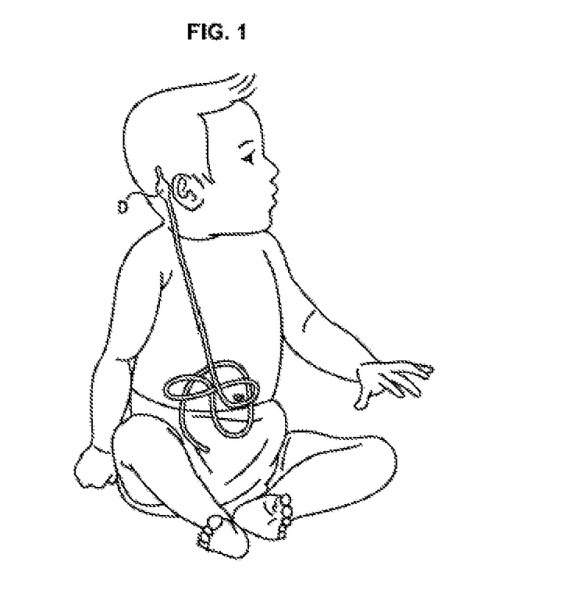
FIG. 1 illustrates a child on which a ventriculoperitoneal shunt has been placed.

FIG. 1 shows a child on which a ventriculoperitoneal shunt S has been placed.

Figure 2:
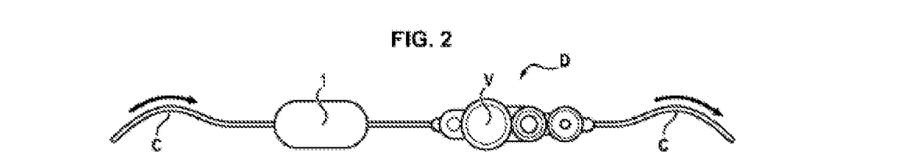
FIG. 2 schematically shows a shunt valve and, upstream thereof, an implantable device in accordance with a possible embodiment for the invention.

As illustrated in FIG. 2, this shunt S generally consists of catheters C upstream and downstream of a valve V which opens to ensure flow of excess cerebrospinal fluid when the intracranial pressure increases.

This same FIG. 2 further shows a device 1 forming a pressure sensor which is implanted upstream of the shunt S.

Figure 3:
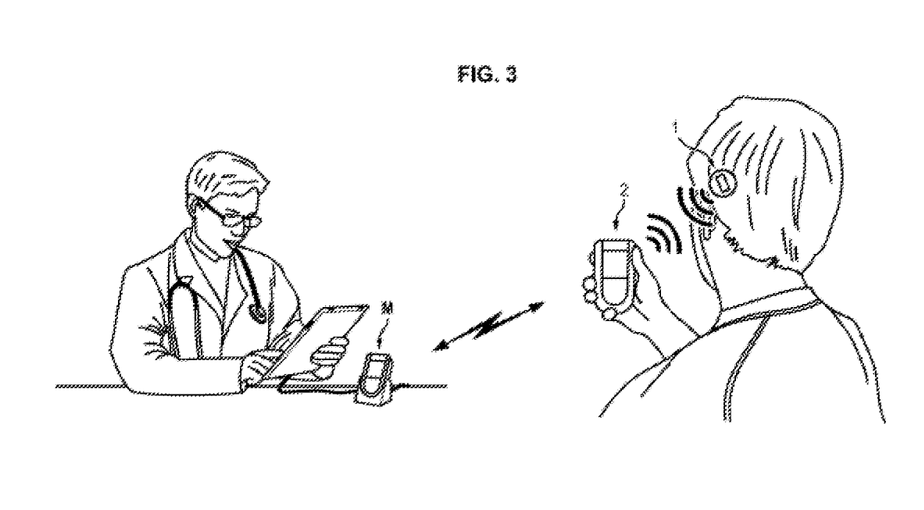
FIG. 3 diagrammatically illustrates the interaction between such an implantable device and an external reader.

As illustrated in FIG. 3, this device 1 is intended to communicate with an external reader 2.

This reader 2 itself integrates communication means allowing it to exchange with remote means M to a doctor (reader similar to reader 2, itself connected to a tablet or more generally to computer means (PC, server of a network, etc.) allowing to process and store the various information read by the readers 2 and transmitted to the means M). This reader 2 used by the patient can also be brought back by the latter to the practitioner in order to be able to download all the data recorded by the patient, via computer links (USB, Bluetooth . . . ) and thus make a diagnosis.

The device 1 is in a rigid or semi-rigid form (FIG. 4) or in the form of a flexible enclosure. It can be separated from the valve V or on the contrary be integrated with the valve in the same flexible enclosure or the same housing, to form a single assembly.

Figure 4:
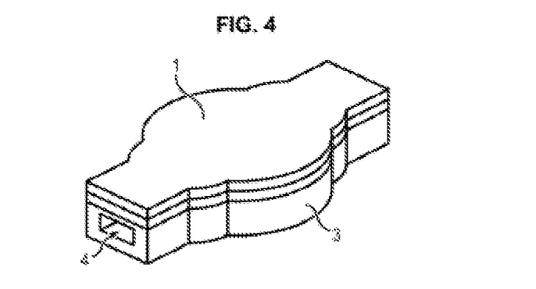
FIG. 4 schematically shows, in perspective view, an implantable device of the type shown in FIG. 2, this device being in the present case of a type made by 3D printing.

It has dimensions similar to those of the shunt S, i.e. approximately 47×17×10 mm$^3$ (indications given as an order of magnitude).

Figure 5A:
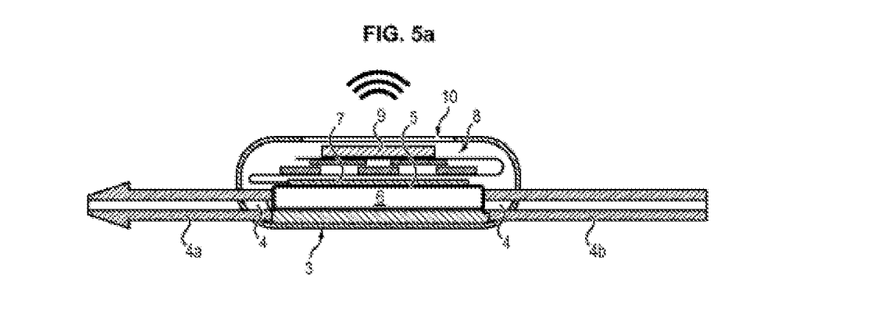
FIGS. 5a and 5b, on the one hand, and 6a and 6b, on the other hand, illustrate two other possible embodiments for such an implantable device.
Figure 5B:
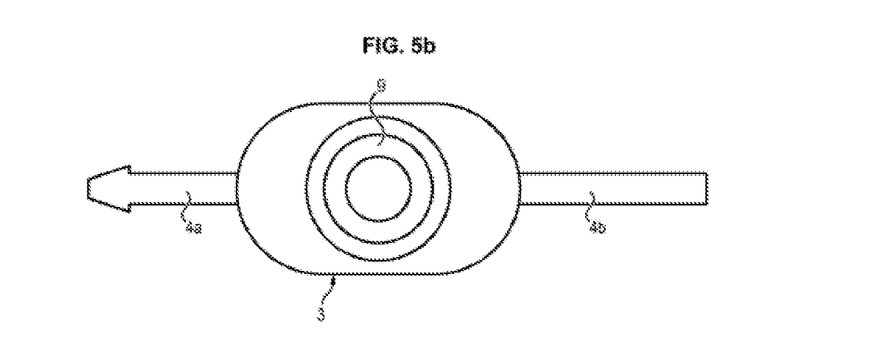

As illustrated in FIGS. 4, 5a and 5b, as well as 6a and 6b, different configurations are possible for said sensor 1.

In the examples illustrated in these figures, it is for example in the form of a structure which includes:
- a semi-rigid or rigid housing 3,
- a channel 4 which passes through the housing 3 and which allows a laminar circulation of the cerebrospinal fluid, avoiding stagnation of the CSF that can cause infections and obstructions, a flexible separation membrane 5 which closes the channel 4 and which is for example made of the same material as the housing 3,
a measuring chamber 6,
a piezoelectric or piezoresistive sensor 7 arranged in said chamber 6 and added onto the membrane 5,
a circuit 8 with different electronic components,
an antenna 9 which is integrated to said circuit or connected thereto.

The membrane 5 and the housing 3 are made of one or several biocompatible material(s).

For example, said housing 3 and the membrane 5 may be made of silicone and/or parylene based-hydrophobic polymeric materials optionally covered with a polytetrafluoroethylene-based material (PTFE or Teflon®).

The membrane 5—and more generally—the totality of the inner walls of the chamber may be covered with parylene to allow perfect seal and prevent particles from being caught during the flow of CSF fluid in the chamber 6.

In the case where the housing 3 is rigid, it may be made of biocompatible metals (titanium) or ceramics.

For example, the housing may be mostly made of titanium with at least one electromagnetic wave-transparent ceramic window 10 to allow communication with the outside.

The circulation channel 4 which passes through said housing 3 is adapted for a connection to a shunt of said fluid upstream of the valve. In particular, it opens into the measuring chamber 6, on its both sides. It ensures circulation of the shunted fluid through said chamber 6 and said housing 3.

It is for example constituted by an upstream end-piece 4a and a downstream end-piece 4b which each open into the chamber 6 and allow, in their portion external to the housing, a connection to catheters of the shunt circuit. The end-pieces 4a and 4b are of a type allowing connection to any type of valve (adjustable, at constant rate and constant pressure), regardless of the supplier.

The end-piece 4b is for example directly connected to the valve, which avoids putting back a catheter tip between the device and the valve and avoids introducing a disturbance in the circulation of the CSF.

The membrane 5 which carries the sensor 7 may be insulated therefrom by a layer forming a titanium insulation barrier.

The measuring chamber 6 has general rounded shapes devoid of angle, in order to limit the flow disturbances for the CSF fluid.

The chamber 6 has for example a flat circular shape or a generally elongated ellipsoid shape.

The channel 4 opens into said chamber 6 at two diametrically opposite ends.

The sensor 7 is a Si membrane sensor, which is for example of the type described in the patent application WO2014187937, other types of sensors being nevertheless possible.

It has a shape and dimensions complementary to those of the measuring chamber 6 and is for example constituted by a disc of 1 cm in diameter and 50 μm in thickness carrying one or more electrode(s) in the center or on the periphery.

The circuit 8 may be a flexible printed circuit.

It can carry the antenna 9, which is then for example a coil antenna as will be described later in more detail (FIGS. 5a and 5b).

Figure 6A:
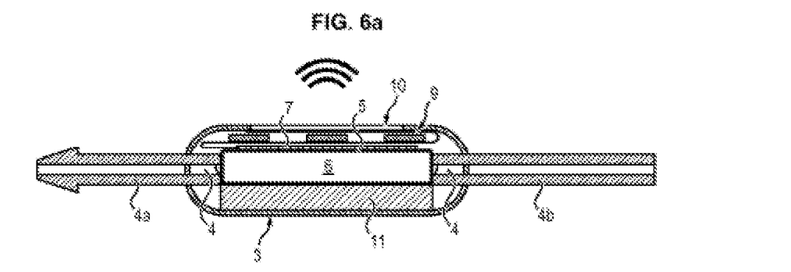
Figure 6B:
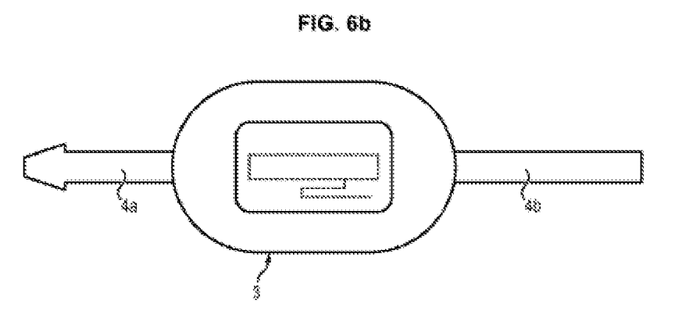

Alternatively, the antenna 9 may be carried by a single-sided PCB circuit bonded to the housing 3, on an inner face thereof (FIGS. 6a and 6b). Different architectures are possible for the piezoelectric sensor 7 inside the device 1.

In a first variant, the piezoelectric sensor can operate in a passive mode (appearance of the load under the effect of a deformation) by being associated with an amplifier at the electronics 8.

The pressure measured by the sensor 7 and read by the reader 2 is then analyzed to deduce therefrom, when appropriate, the existence of an overpressure in the circulation channel 4. Particularly, the higher the pressure therein, the more the flexible membrane 5—which is deformed—becomes rigid. The collected signal (which corresponds to the heartbeat) is attenuated.

The analysis of this signal can be made at the reader 2 or remotely, via the computer means associated with the reader M with which said reader 2 communicates. The attenuation level can be compared to a previously determined threshold for each patient. The detection of the crossing of this threshold may for example trigger the emission of an alert signal to the user of the reader.

In another variant, the piezoelectric sensor 7 can be resonantly biased by the electronics 8 in a dynamic mode.

The reader 2 or the remote apparatus then analyzes the variation of the resonance frequency of the sensor. The existence of an overpressure in the channel 4 will indeed cause a shift in the resonance frequency of the flexible membrane. The variation of the resonance frequency is for example also compared to a threshold which, when crossed, triggers the emission of an alert signal.

In the modes requiring excitation of the sensor, the electrode of the sensor is central while the reading electrodes are on the edge of the piezoelectric structure.

In still other variants, the excitation electrodes may be located on the side opposite to the fluid circulation channel 4.

Different implantations are possible for the device 1.

Figure 7A:
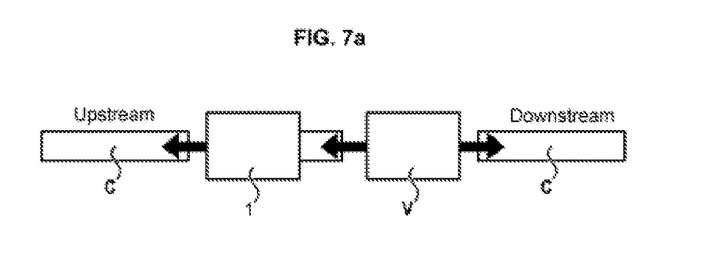
FIGS. 7a and 7b illustrate two examples of possible implantation configurations.

In particular, as illustrated in FIG. 7a, the device 1 can be arranged in series with the valve V between both upstream and downstream catheters C.

Figure 7B:
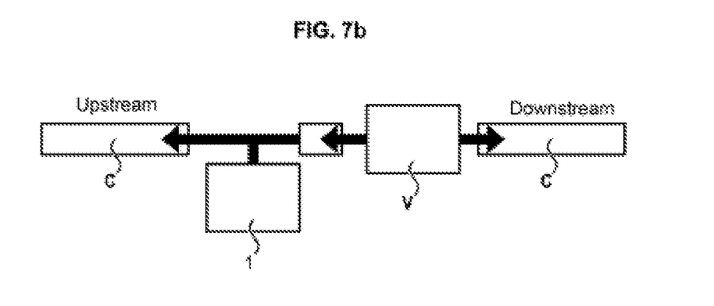

It can also be arranged as a shunt (FIG. 7b).

With these different implantations, the device 1 is adapted to measure, thanks to the piezoelectric sensor 7, an overpressure upstream of the shunt S.

The triggering of a measurement by the sensor 7 can be controlled by interrogation by the reader 2. The electronics 8 manages the exchanges with the reader 2 and controls the actuation of the measurement by the piezoelectric sensor 7.

Figure 8A:
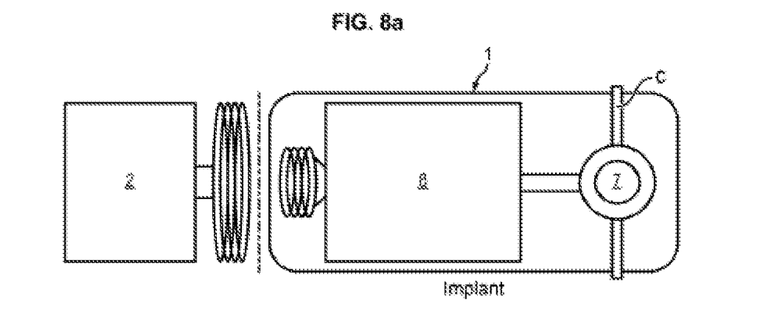
FIGS. 8a and 8b schematically illustrate two types of communication electronics that can be envisaged.

As illustrated in FIG. 8a, the electronics 8 can comprise a remote power system 9 which allows eliminating the need for an embedded cell and gives the device a long service life.

Such a cell-free inductive system then operates preferably in the 13.56 MHz, 27 MHz frequency bands (ISM frequency bands). The antenna 9 is then a coil antenna which is for example arranged on the flexible circuit 8 (embodiment of FIGS. 5a and 5b).

As a variant (FIG. 6a and FIG. 8b), the electronics 8 can integrate a rechargeable cell 11 or battery, which allows greater ranges between the reader 2 and the implanted device 1, the latter integrating a radio frequency communication electronics.

Figure 8B:
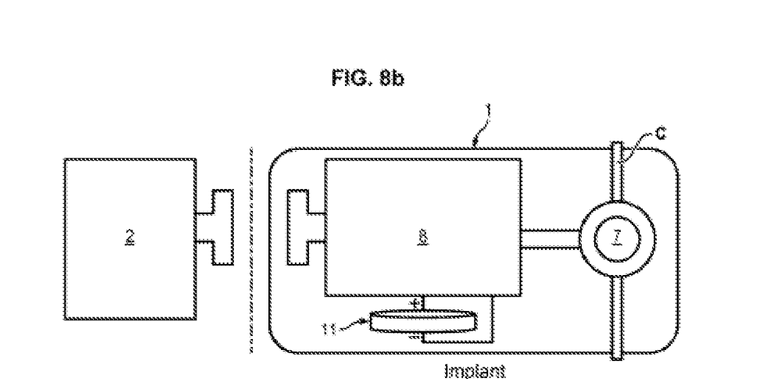

This variant also allows programming repetitive measurements without intervention by taking pressure in a semi-continuous manner.

In this embodiment, the reader 2 wakes up the implant (by means of a radio frequency signal, including a digital pairing signature and emitted in the 2.4 GHz frequency band) constituted by the sensor 1 by requesting a measurement, then said implant returns to the standby mode after having transmitted the result of the measurement, in order to save battery.

Such a cell-operated device operates in the reserved frequency bands 402 MHz (MICS band) or 433 MHz (ISM band).

As a further variant, the device 1 can integrate sensors other than piezoelectric-type measuring sensors: sensors able to measure the pH or to perform a biochemical analysis of the CSF to detect an infection, etc.

Figure 9:
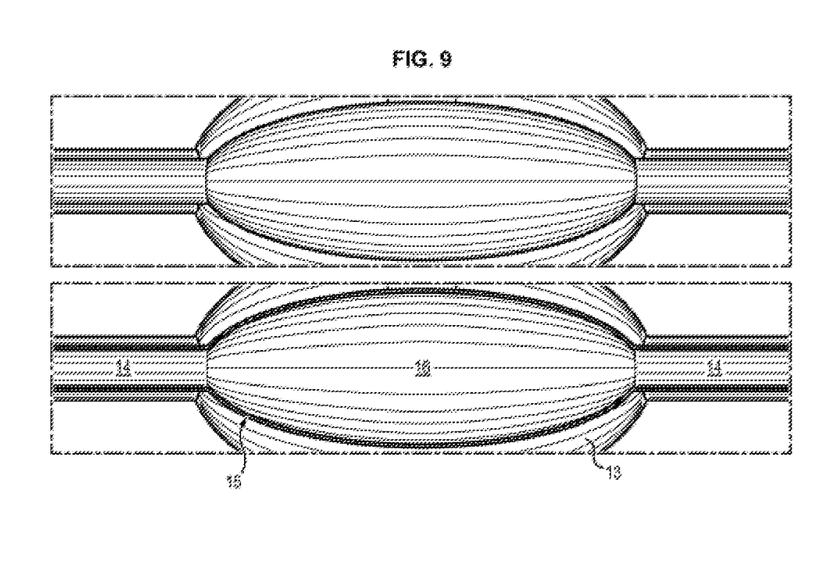
FIG. 9 illustrates another example of a measuring chamber.

FIG. 9 shows a possible measuring chamber variant.

In this variant, the chamber—referenced 16—has a generally elongated ellipsoid shape. It is arranged and defined by a shell 13 independent of the housing where the electronics is located.

This shell 13 is constituted by two assembled rigid half-shells.

Each of these half-shells is extended by an opening 14, both openings 14 constituting the inlets and outlets for the CSF fluid.

These half-shells and the inlet/outlet openings are for example made of titanium or a ceramic.

The dimensions of the chamber 16 are for example the following:
diameter of the major axis in the CSF fluid circulation direction: 13 mm,
diameter of the major axis in its middle plane: 6 mm,
diameter of the major axis in its middle plane: 5 mm A flexible membrane 15 is provided, which covers the entire interior of the chamber 16 as well as the interior of both inlet and outlet openings 14.

This membrane 15 is for example made of a silicone and/or parylene-based polymeric material possibly covered with a polytetrafluoroethylene (PTFE or Teflon®) or parylene-based material.

Its thickness is comprised between 1000 nm and 100 nm for parylene and comprised between 100 µm and 900 µm for silicone.

Such a membrane arrangement, in which said membrane covers the entire interior of the chamber 16, ensures perfect seal and separation between the circulation of the CSF fluid and the electronics of the device.

In addition, it contributes to avoiding any asperity for the CSF fluid circulating in the chamber 16, thus avoiding the risk of deposit and clogging.

Figure 10:
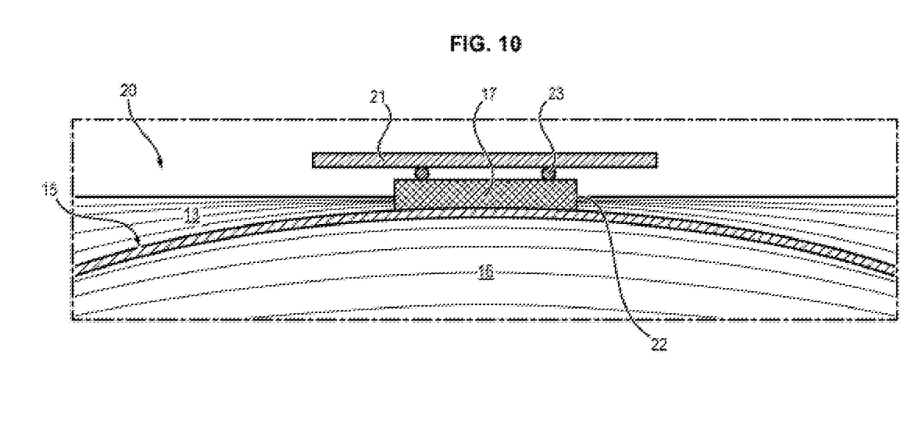
FIG. 10 illustrates a mode of possible placement of the sensor on the chamber and its membrane.

As illustrated in FIG. 10 and the following figures, the shell 13 is mounted inside a housing 20, itself independent of the housing where the electronics is located.

This housing 20 integrates a rigid or semi-rigid printed circuit 21, which is fixed inside said housing 20 and which carries a pressure sensor 17, for example of the piezoelectric or piezoresistive type.

A hole 22 is provided for this purpose in the shell 13. This hole 22 passes through the thickness of said housing in order to allow the sensor 17 to be in contact with the membrane 15. When appropriate, the sensor 17 itself includes a measuring membrane and the pressure transfer between this membrane and the membrane 15 occurs through an intermediate pin or through a gel or more generally any incompressible inert material.

The sensor 17 and the hole 22 have for example the dimensions 1×1 mm.

It should be noted that the thus performed mounting allows perfect separation between, on one side, the electronics and, on the side, the circulating CSF fluid, while allowing the sensor to be mounted on the membrane, which provides greater measurement accuracy.

Figure 11A:
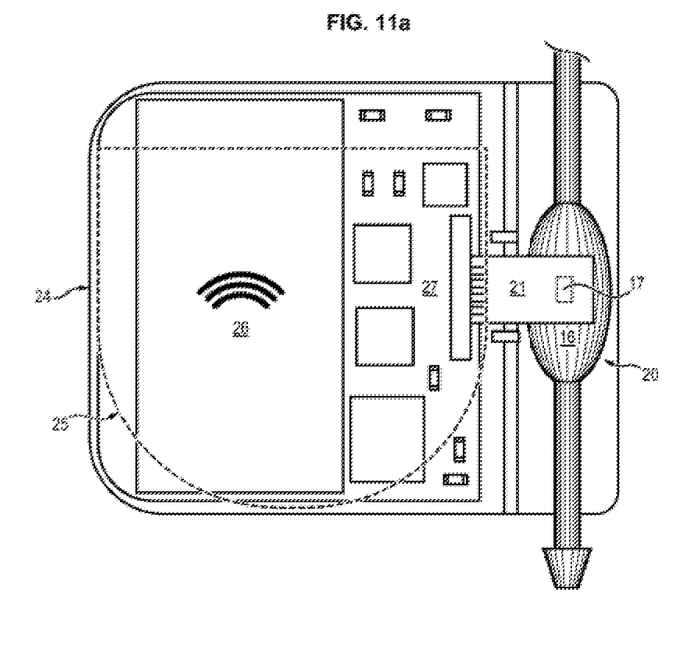
FIGS. 11a and 11b illustrate another possible embodiment of the device of the invention.
Figure 11B:
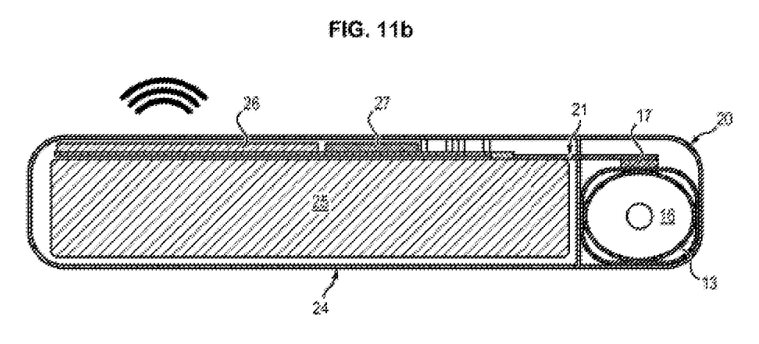

The mounting of the housing 20 on the electronics housing (referenced 24) is more particularly illustrated in FIGS. 11a, 11b.

The electronics housing 24 integrates a battery 25, a planar antenna 26 and a flex circuit 27 on which the various electronic components are mounted.

Figure 12A:
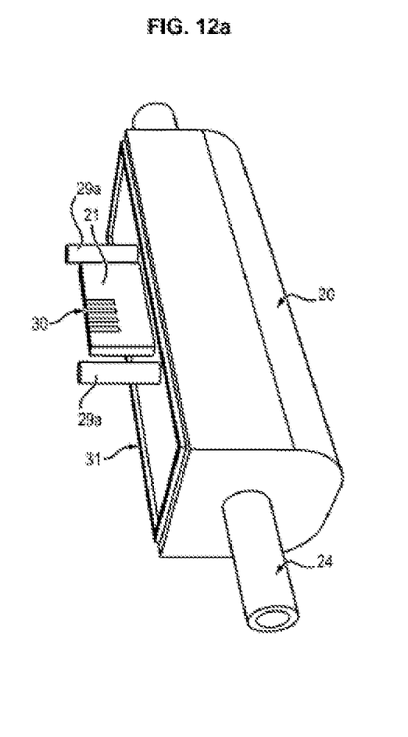
FIGS. 12a and 12b illustrate the mechanical and electronic connections of this other embodiment.
Figure 12B:
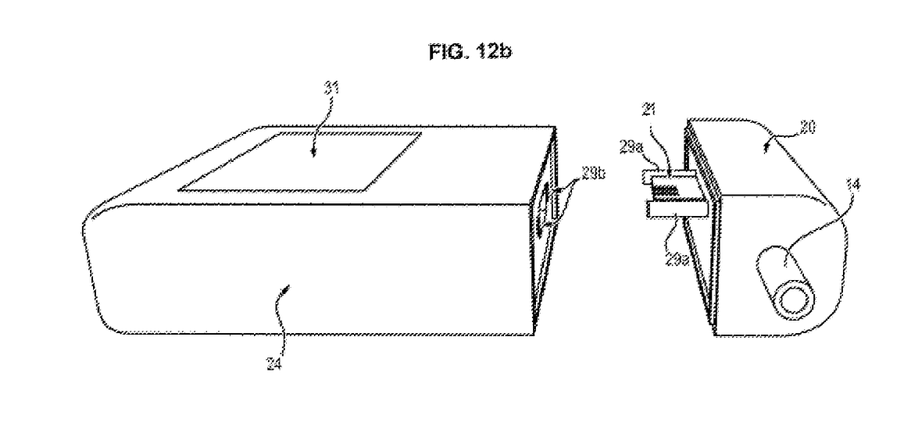

The housing 20 is mechanically and electronically connected to the housing 24 in the manner illustrated in FIGS. 12a, 12b.

As more particularly visible in these figures, the rigid printed circuit 21 extends outside the housing 20 and is intended to engage in a complementary guide slot 28 presented in the housing 24.

A closure 31 allows the shell 13, the sensor 17 and the circuit 21 to be initially mounted in the housing 20. This closure 21 ensures seal of the housing 20 once the assembly is placed.

Spikes 29a and complementary orifices 29b are also provided on the housing 24 or the housing 20 to ensure guiding and foolproofing when placing the housing 24 on the housing 20.

Contacts 30 are provided at the edge of the board 21 which cooperate with complementary contacts of the flex circuit.

Thus, the electronics housing 24 is easily connected and disconnected compared to the housing 20. It can be changed without requiring intervention and modification at the implant itself, the latter remaining plugged in the cerebrospinal fluid circulation circuit while the electronic portion and the battery are changed. As the unplugging of CSF circulation catheters does not occur, the risk of infection related to this unplugging is therefore eliminated.

FIG. 12b also shows a ceramic window 31 formed on the housing 24 for the emission/reception of the antenna (titanium housing 24).

The invention claimed is:

1. A device for detecting malfunction of a valve/catheters assembly for shunting a cerebrospinal fluid, including:
a chamber (6, 16);
a laminar channel (4, 14) which opens into said chamber (6, 16), on its both sides, and which is adapted to ensure circulation of a shunted fluid, through said chamber (6, 16);
a pressure measuring sensor (7, 17) for measuring a pressure in said chamber (6, 16);
a flexible membrane (5, 15) which separates the sensor (7, 17) from the chamber (6, 16);
a control and communication electronics (8, 9) able to exchange with an external reader in order to transmit an ambulatory measurement by said sensor (7, 17),
the sensor (7, 17) being added onto the flexible membrane (5, 15) with which it is in contact,
characterized in that the walls of the chamber are defined by a rigid housing or a shell, the membrane (5, 15) covering the totality of the walls of said chamber (6, 16), the device being able to be implanted upstream of an intracranial valve of a shunt assembly for direct measurement of the intracranial pressure by the pressure sensor.

2. The device according to claim 1, wherein the chamber (6, 16) is defined by a shell (13) of a generally elongated ellipsoid shape, said shell (13) being traversed by a hole (22) allowing to put the sensor (7, 17) into contact with the membrane (5, 15).

3. The device according to claim 1, characterized in that the flexible membrane is a silicone and/or parylene-based material.

4. The device according to claim 1, characterized in that the membrane is covered with parylene and/or PTFE.

5. The device according to claim 1, characterized in that it includes a titanium layer interposed between the flexible membrane and the sensor.

6. The device according to claim 1, characterized in that an incompressible inert material is interposed between the flexible membrane and a membrane of the sensor.

7. The device according to claim 6, characterized in that a pin or a gel is interposed between the flexible membrane and a membrane of the sensor.

8. The device according to claim 1, characterized in that the control and communication electronics can be mounted/demounted independently of the chamber and is adapted for a mounting/demounting without interruption of the cerebrospinal fluid circulation.

9. The device according to claim 8, characterized in that the shell extends in a housing, said housing being adapted to be mounted on a housing receiving control and communication electronics.

10. The device according to claim 9, characterized in that sensor is mounted on a rigid board which extends, on one side, inside the housing receiving the shell of the chamber and, on the other side, outside said housing, said rigid board having, on its portion outside said housing, contacts for the electronic connection with the housing receiving the control and communication electronics.

11. The device according to claim 9, characterized in that both housings include spikes and complementary guide/foolproof orifices.

12. The device according to claim 9, characterized in that the housing includes a ceramic window to allow passage of electromagnetic waves.

13. An assembly including a device according to claim 1 and a reader adapted to communicate with the control and communication electronics of the sensor.

* * * * *